United States Patent
Tsudome et al.

(10) Patent No.: US 7,695,684 B2
(45) Date of Patent: Apr. 13, 2010

(54) MICRO FLUIDICS SYSTEM AND TREATING METHOD USING SAME

(75) Inventors: Hidekazu Tsudome, Ryugasaki (JP); Takehiko Kitamori, Kawasaki (JP); Manabu Tokeshi, Kawasaki (JP)

(73) Assignee: Hitachi Plant Technologies, Ltd. (JP)

( * ) Notice: Subject to any disclaimer, the term of this patent is extended or adjusted under 35 U.S.C. 154(b) by 988 days.

(21) Appl. No.: 11/138,373

(22) Filed: May 27, 2005

(65) Prior Publication Data

US 2005/0263398 A1 Dec. 1, 2005

(30) Foreign Application Priority Data

May 28, 2004 (JP) .............................. 2004-159110

(51) Int. Cl.
*B01L 3/02* (2006.01)
(52) U.S. Cl. .................. 422/100; 422/63; 422/68.1; 422/81; 422/103
(58) Field of Classification Search ................. 422/100, 422/63, 68.1, 81, 103
See application file for complete search history.

(56) References Cited

U.S. PATENT DOCUMENTS 6,063,339 A * 5/2000 Tisone et al. ................... 422/67

2001/0036669 A1* 11/2001 Jedrzejewski et al. ......... 436/94

FOREIGN PATENT DOCUMENTS

| JP | 08-178897 | 7/1996 |
| JP | 2003-114229 | 4/2003 |
| JP | 2004-531369 | 10/2004 |
| WO | WO 0078456 A1 * | 12/2000 |
| WO | WO 02/064243 | 8/2002 |

* cited by examiner

*Primary Examiner*—Lyle A Alexander
*Assistant Examiner*—Dennis M White
(74) *Attorney, Agent, or Firm*—Antonelli, Terry, Stout & Kraus, LLP.

(57) ABSTRACT

For enlarging the application range of samples capable of being treated, decreasing the amount of samples used, preventing deterioration of samples by a change with the passage of time and preventing mixing of samples by diffusion, a micro fluidics system according to the present invention comprises a sample server which stores plural samples and which has sample efflux portions, a microchip for feeding samples to a treating portion through plural sample introducing portions communicating with the sample efflux portions and further through a microchannel, allowing the samples to be subjected to a predetermined treatment, and a sample feeder for feeding the samples stored in the sample server to the sample introducing portions through the sample efflux portions. The sample feeder comprises valves for opening and closing communication paths between the sample efflux portions of the sample server and the sample introducing portions of the microchip and pressurizing devices for pressurizing the samples stored in the sample server and pushing them out into the sample introducing portions in an open condition of the valves.

9 Claims, 6 Drawing Sheets

MICRO FLUIDICS SYSTEM AND TREATING METHOD USING SAME

CLAIM OF PRIORITY

The present application claims priority from Japanese application serial JP 2004-159110 filed on May 28, 2004, the content of which is hereby incorporated by reference into this application.

FIELD OF THE INVENTION

The present invention relates to a micro fluidics system and a treating method using the same. Particularly, the present invention is suitable for a micro fluidics system having a microchip for treating a sample and a treating method using the micro fluidics system.

BACKGROUND OF THE INVENTION

Integration techniques for performing chemical reactions in a very small space are being spotlighted from the standpoint of speed-up of chemical reactions, as well as reaction and analysis using a very small amount of sample. In a microchemical system using a microchip, which is one of chemical reaction integrating techniques, there are provided an inlet port for introducing a sample into the microchip and a microchannel connected to the inlet port. Within the microchannel there are performed such sample treatments as reaction, separation, extraction, detection, mixing, synthesis, and analysis. As examples of reactions performed in the microchemical system there are diazotization reaction, nitration reaction and antigen-antibody reaction. As examples of extraction and separation there are solvent extraction, electrophoretic separation and column separation.

In an electrophoretic apparatus described in Patent Literature 1, a plate member is formed integrally by bonding first and second substrates, a groove for analysis provided with a buffer sump and a groove for sample injection are formed in both end portions of the first substrate, a through hole is formed in the second substrate at a position opposed to the buffer sump in the first substrate, and an electrode film for the application of voltage is formed on an inner wall of the through hole and also around both sides of the through hole. In this electrophoretic apparatus, connection is made through the electrode film to a high voltage source installed in the body of the apparatus to effect the application of voltage, allowing migration to take place.

Another conventional micro fluidics system has been proposed for example in Japanese Patent Laid-Open No. 2003-114229 (Patent Literature 2) in which a sample is conveyed to a microchip or a microplate with use of a syringe pump.

A measuring analysis equipment using a microchip in Patent Literature 2 has a microchip, the microchip being provided with a first very small channel for allowing a sample to flow therethrough, a second very small channel for allowing a marker substance to flow therethrough, a very small reaction channel formed by a combination of the first and second channels, and a reactive site provided in the reaction channel and with a specific binding substance fixed thereto. A syringe pump is connected through a silicon tube to the first and second channels in the microchip and both sample and marker substance are fed from the syringe pump.

Patent Literature 1: Japanese Patent Laid-Open No. H8(1996)-178897

Patent Literature 2: Japanese Patent Laid-Open No. 2003-114229

SUMMARY OF THE INVENTION

In Patent Literature 1, since an electrophoretic method is used as a sample conveying method, fluids capable of being handled in the same method are limited to aqueous solutions which can migrate upon application of voltage thereto. It has so far been impossible to handle such samples as non-polar organic solvents.

In Patent Literature 2, since the silicon tube connected from the sample conveying syringe pump to the microchip is much larger than the very small channel in the microchip, it has been necessary to use a large amount of sample for filling the interior of the tube which provides connection from a pump discharge port to a sample inlet port of the microchip. Moreover, since the retention time of the sample within the tube becomes longer, there has been a fear of the sample quality being deteriorated by a change with the passage of time. Further, at the tip of the tube the sample is in contact with another sample at all times and so there has been the problem that there occurs mixing of samples by diffusion even without operation of the pump.

It is an object of the present invention to provide a micro fluidics system able to expand an application range of samples capable of being treated by the system, decrease the amount of each sample used, prevent deterioration of a sample by a change with the passage of time and prevent mixing of plural samples by diffusion, as well as a treating method using the micro fluidics system.

According to the present invention, for achieving the above-mentioned object, there is provided a micro fluidics system comprising a sample server which stores a plurality of samples and which has sample efflux portions, a microchip for feeding samples to a treating portion through a plurality of sample introducing portions communicating with the sample efflux portions and further through a microchannel communicating with the sample introducing portions, allowing the samples to be subjected to a predetermined treatment, and a sample feeder for feeding the samples stored in the sample server to the sample introducing portions through the sample efflux portions, wherein the sample feeder comprises valves for opening and closing communication paths between the sample efflux portions of the sample server and the sample introducing portions of the microchip and pressurizing devices for pressurizing the samples stored in the sample server and pushing them out into the sample introducing portions in an open condition of the valves.

The following are more preferred constructions related to the above construction according to the present invention.
(1) The valves are provided so as to open and close openings of the sample introducing portions.
(2) The sample server includes cylindrical bodies whose one ends are open larger than the sample introducing portions and whose opposite ends are closed, the cylindrical bodies being installed so that the one ends thereof come into abutment against the microchip, allowing the openings thereof to cover the openings of the sample introducing portions, and the valves are positioned within the sample server to open and close the openings of the sample introducing portions and are installed so as to come into abutment against the surface of the microchip.
(3) A fluid feed control mechanism having a drive portion is provided, the drive portion using a drive source of the valves and a drive source of the pressurizing devices in common.
(4) The sample server includes cylindrical bodies which are open on both sides thereof, the pressurizing devices include partition plates which close one open sides of the cylindrical bodies and which are disposed movably and operating members extending from the partition plates to the exterior of one openings of the cylindrical bodies, the valves include valve bodies disposed on the other opening sides of the cylindrical bodies and operating members extending from the valve bodies to the exterior of the other openings of the cylindrical bodies through the partition plates, and the fluid feed control mechanism includes the foregoing drive portion which actuates the operating members of the pressurizing devices and the operating members of the valves in an alternate manner.

(5) A drain for storing the samples treated by the microchip is attached to the microchip.

(6) The microchip includes a plurality of independent treatment paths each constituted by the sample introducing portions, the microchannel and the treating portion.

(7) The microchip is formed by a multitude of independent rows of the treatment paths and the sample server is formed independently and correspondingly to each of the rows of the treatment paths, is supported through a common connecting member and is installed in the microchip removably.

According to the present invention, for achieving the foregoing object, there also is provided a treating method using a micro fluidics system, comprising installing in a microchip a sample server which stores a plurality of samples, in a of closing communication paths condition between sample efflux portions for the samples in the sample server and a plurality of sample introducing portions in the microchip by means of valves, opening the valve concerned between the associated sample efflux portion in the sample server and the associated sample introducing portion in the microchip, allowing the sample efflux portion and the sample introducing portion to communicate with each other, pressurizing a sample by means of pressurizing devices, feeding the pressurized sample from the sample efflux portion to the sample introducing portion, a microchannel and a treating portion in this order, allowing the sample to be treated in the treating portion, closing the open valve, thereafter opening the valve concerned between another associated sample efflux portion in the sample server and another associated sample introducing portion in the microchip, allowing the sample efflux portion and the sample introducing portion to communicate with each other, pressurizing another sample by pressurizing devices, feeding the pressurized sample from the sample efflux portion to the sample introducing portion, the microchannel and the treating portion in this order, and allowing the sample to be treated in the treating portion.

The following is a more preferred construction related to the above construction according to the present invention. (1) All of the valves are brought into a closed condition and a treatment path formed by the sample introducing portions, the microchannel and the treating portion is evacuated from an efflux side of the treating portion.

According to the present invention it is possible to provide a micro fluidics system able to expand an application range of samples capable of being treated by the system, decrease the amount of each sample used, prevent deterioration of a sample by a change with the passage of time and prevent mixing of plural samples by diffusion, as well as a treating method using the micro fluidics system.

DETAILED DESCRIPTION OF PREFERRED EMBODIMENTS

Plural embodiments of the present invention will be described hereinunder with reference to the drawings. In connection with the following embodiments, the same reference numerals in the drawings represent the same or equivalent portions.

A micro fluidics system and a treating method using the same according to a first embodiment of the present invention will be described below with reference to FIGS. 1 to 4.

An entire construction of a micro fluidics system 100 according to this first embodiment will first be described below with reference to FIG. 1, which is a construction diagram showing the micro fluidics system of this embodiment.

The micro fluidics system 100 is made up of a microchip device 50, sample servers 4, pressuring devices 15, valves 18, a fluid feed control mechanism 5, a temperature controller 7, a treatment condition detector 8, and a stage 6. Treatments performed in the micro fluidics system 100 include reaction, separation, extraction, detection, mixing, synthesis and analysis of samples. Examples of the reaction include diazotization reaction, nitration reaction and antigen-antibody reaction. Examples of the extraction and separation include solvent extraction and column separation. The pressurizing devices and the valves 18 constitute a sample feeder.

The microchip device 50 includes a microchip 1, a holder 2, a drain 9 and a base 3. The microchip device 50 is placed on the stage 6. The microchip 1 is inserted by sliding between the holder 2 and the base 3 from the right side in FIG. 1. The drain 9 is for the storage of sample after being reacted within the microchip 1 and is in communication with an outlet side of a channel separating portion 10b (see FIG. 2). The drain 9 is provided with a fluid discharge port 9a (see FIG. 4) so as to permit the discharge of sample to the exterior.

The temperature controller 7 includes a Peltier element and a temperature sensor. The temperature controller 7 is provided for controlling the temperature of sample to a temperature necessary for performing such a treatment as reaction, extraction or separation within the microchip device and is disposed between the microchip 1 and the stage 6. The Peltier element has a heating or cooling function, provided the use of a mere heater will do in the case where only heating suffices. The temperature sensor is for detecting the temperature of the microchip device 50. The Peltier element is controlled on the basis of the result of measurement conducted by the temperature sensor to control the temperature of the microchip 1 to a predetermined temperature necessary for the treatment of sample. More specifically, a temperature regulator (not shown) is connected to the temperature sensor to control the supply of electric power for the Peltier element.

The treatment condition detector 8 is used to detect the condition after reaction in a chemical system provided within the microchip 1. There may be provided a moving mechanism for moving the treatment condition detector 8 to a desired position above the microchip device 50.

Next, a concrete construction of the microchip 1 will be described with reference to FIG. 2, which is an explanatory perspective view of the microchip used in the micro fluidics system of FIG. 1.

The microchip 1 is formed in the shape of a plate using, for example, glass, silicon, or plastic. The illustrated microchip 1 is to be used in a micro fluidics system which is for microchips for immunoanalysis. The microchip 1 includes a channel reactor portion 13 which accommodates solid fine particles 11 of not larger than 1 mm in diameter as a reactive solid phase, a microchannel 10 having a sectional area whose width is smaller than the diameter of each solid fine particle 11, plural sample introducing portions 14, and a sample discharge portion 12. The channel reactor portion 13 constitutes a treating portion. The microchannel 10 is made up of a channel introducing portion 10a and a channel separating portion 10b. Sample introducing portions 14a, 14b and the sample discharge portion 12 are open to one-side surface of the microchip 1.

The plural sample introducing portions 14 include a labeled antibody introducing portion 14a for introducing a labeled antibody as a first sample into the channel reactor portion 13 and an antigen introducing portion 14b for introducing an antigen as a second sample into the channel reactor portion 13. The labeled antibody introducing portion 14a and the antigen introducing portion 14b are in communication with the channel reactor portion 13 through the channel introducing portion 10a. The sample discharge portion 12 is in communication with the channel reactor portion 13 through the channel separating portion 10b.

Figure 1:
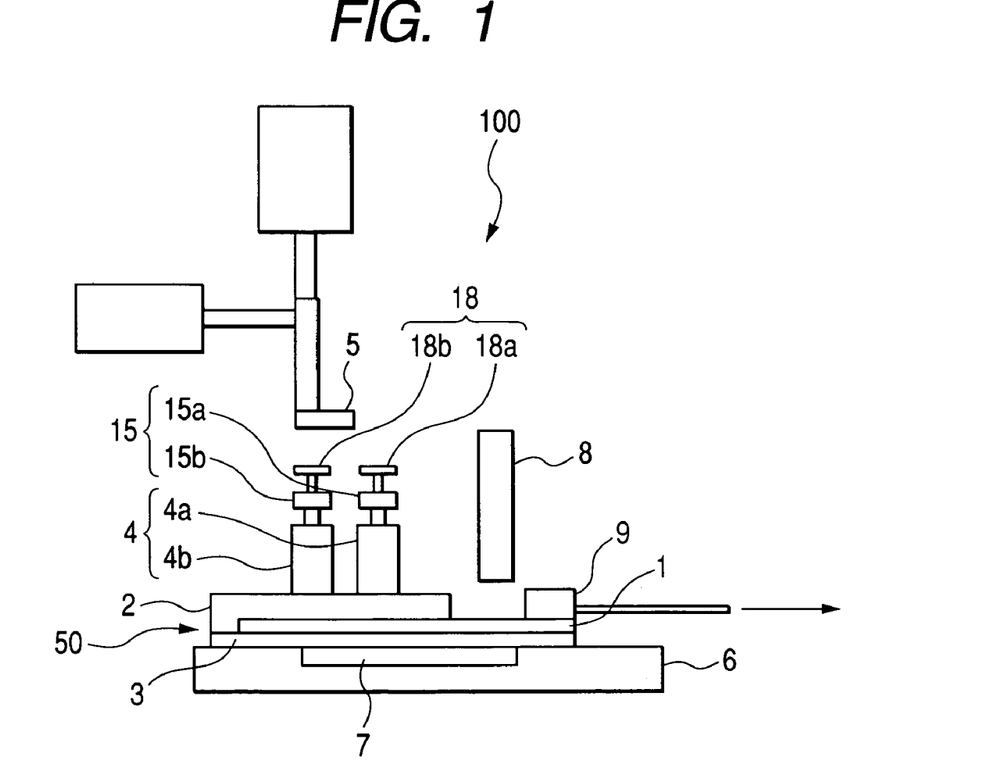
FIG. 1 is a construction diagram showing a micro fluidics system according to a first embodiment of the present invention.
Figure 3:
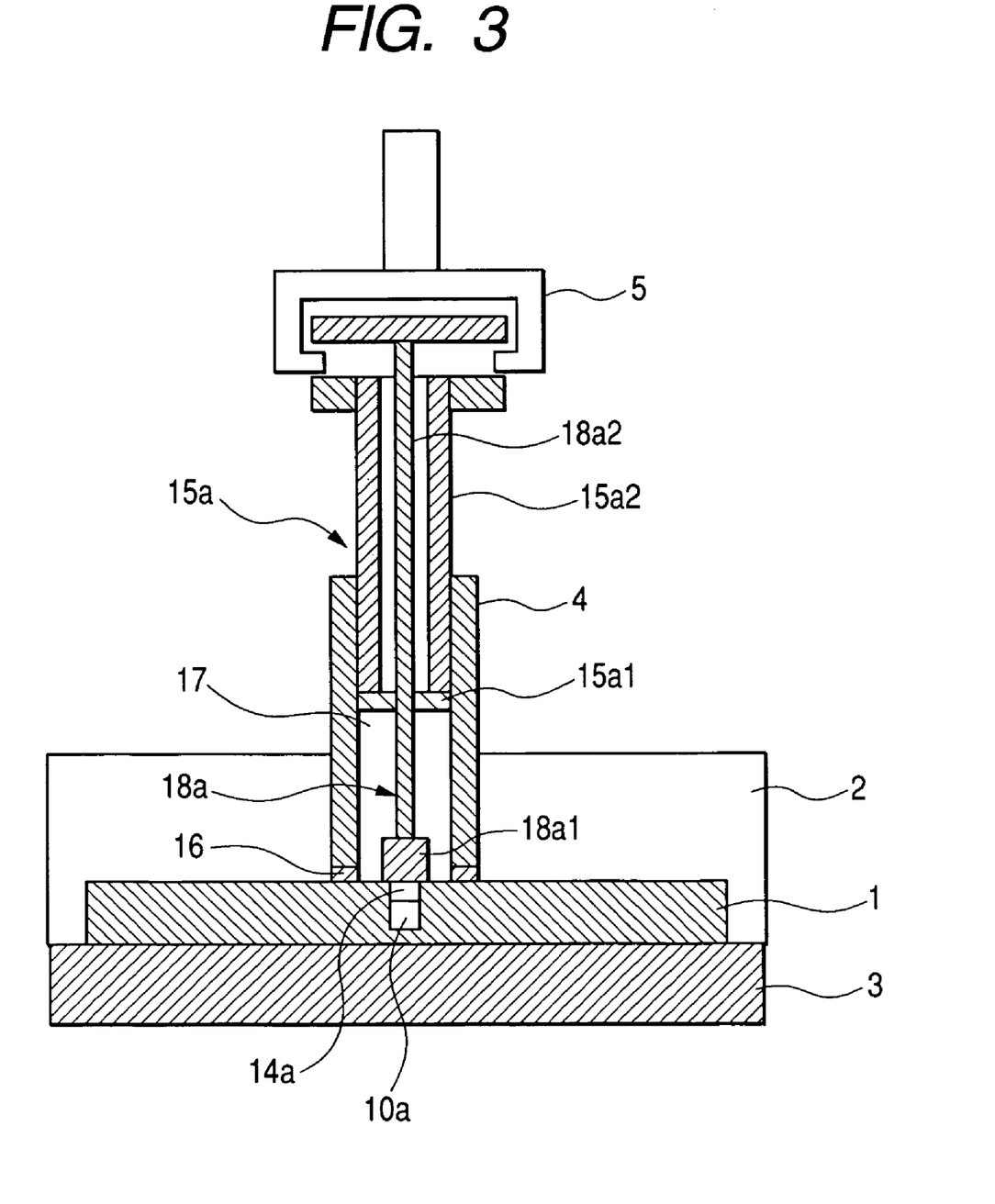
FIG. 3 is a vertical sectional view of a principal portion of the micro fluidics system shown in FIG. 1.
Figure 4:
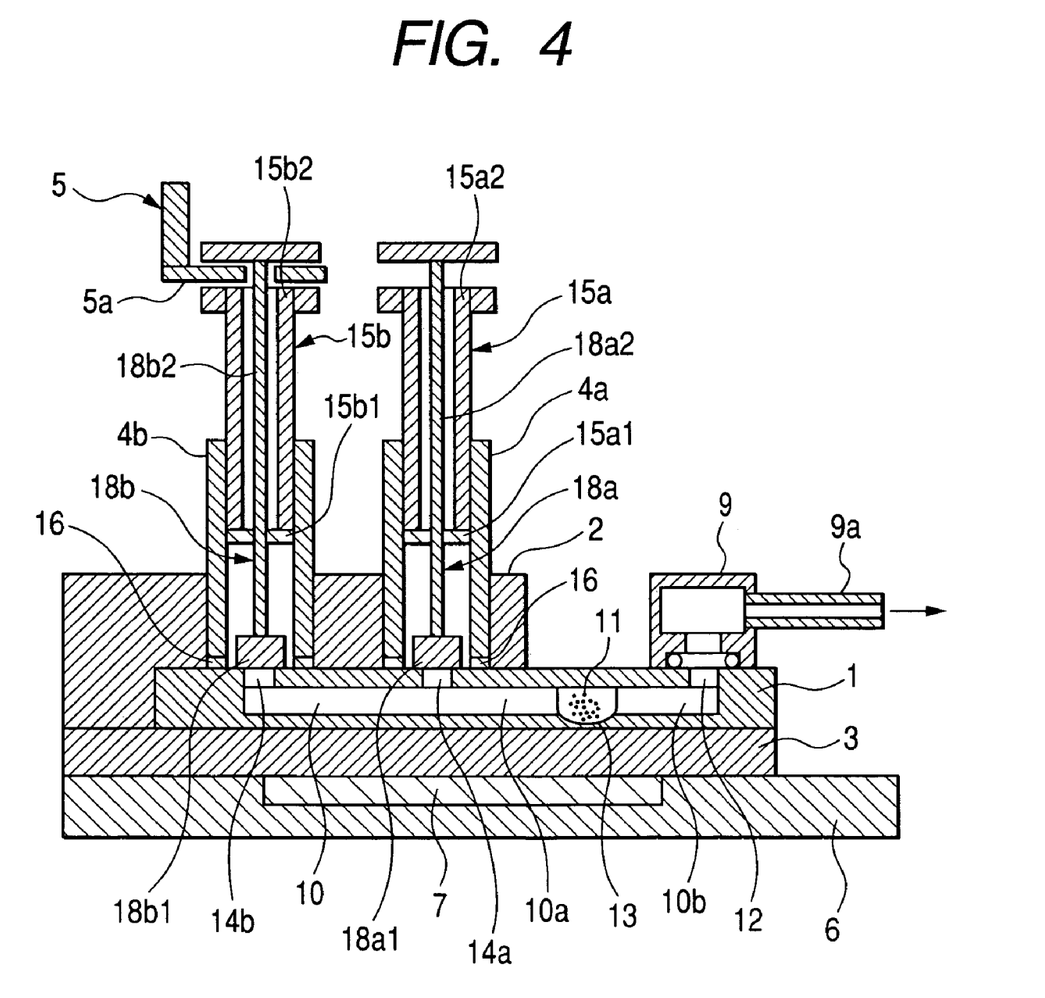
FIG. 4 is a central sectional view of FIG. 3.

Next, a more concrete construction of the micro fluidics system 100 will be described with reference to FIGS. 3 and 4, of which FIG. 3 is a vertical sectional view of a principal portion of the micro fluidics system shown in FIG. 1 and FIG. 4 is a central sectional view of FIG. 3.

The sample servers 4 store plural samples and have sample efflux portions. In this embodiment, the sample servers 4 comprise plural sample servers 4a and 4b, with different kinds of samples being stored in the sample servers 4a and 4b respectively. The sample servers 4a and 4b are formed of a material having chemicals resistance to the samples handled in this embodiment or a material not exerting a bad influence on those samples, e.g., stainless steel, silicone rubber, fluororesin, urethane rubber, peek material, glass, or polycarbonate. The size of each of the sample servers 4a and 4b is set to a size matching a required amount of sample to be injected therein. Although in this embodiment the sample servers 4a and 4b are in the shape of a circular cylinder, any other shape, e.g., elliptic cylinder shape, may be adopted insofar as it is cylindrical.

The sample servers 4a and 4b are constituted respectively by cylindrical bodies whose lower surface sides are open larger than the sample introducing portions 14a, 14b and whose upper surface sides are closed. The lower surface-side openings of the sample servers 4a and 4b are set at a size which, at the atmospheric pressure, permits the samples stored in the sample servers to stay within the sample servers without leakage under the action of a surface tension.

The sample servers 4a and 4b are installed in abutment at one ends of their cylindrical bodies against the surface of the microchip 1 so that their lower surface-side openings cover the openings of the sample introducing portions 14a and 14b.

More specifically, by utilizing the holder 2, the sample servers 4a and 4b are installed in close contact with the sample introducing portions 14a and 14b of the microchip 1.

A packing 16 is disposed between a lower end of the cylindrical body of each of the sample servers 4a, 4b and the surface of the microchip 1 to ensure airtightness. That is, the interiors of the sample servers 14a, 14b and the sample introducing portions 14, 14b are brought into communication with each other in an airtight manner so as to prevent the leakage of samples to the exterior even when the samples present within the sample servers 4a and 4b are pressurized by pressurizing devices 15a and 15b. Further, even when a positional relation between a substrate end portion of the microchip 1 and the microchip introducing portions 14 provided on the microchip 1 is deviated relative to a desired portion due to a fabrication tolerance, the samples can be introduced positively into the microchip 1 if the inside diameter of the packing 16 is set larger than the size of each microchip introducing portion 14 beforehand taking the amount of such deviation into account.

Valves 18 are provided so as to open and close communication paths between the sample efflux portion side of the sample servers 4 and the sample introducing portion side of the microchip 1. The valves 18 comprise valves 18a and 18b disposed for the sample servers 4a and 4b respectively. The valves 18a and 18b comprise valve bodies 18a1 and 18b1 disposed on the lower opening sides of the sample servers 4a and 4b respectively and operating members 18a2 and 18b2 extending from those valve bodies 18a and 18b to the outside of the upper openings of the sample servers 4a and 4b through partition plates 15a1 and 15b1. The valve bodies 18a1 and 18b1 are installed so as to be positioned within the sample servers 4a and 4b to open and close the openings of the sample introducing portions 14a and 14b of the microchip 1 and so as to be put in abutment against the surface of the microchip 1.

Pressurizing devices 15 comprise plural pressurizing devices 15a and 15b provided respectively for the sample servers 4a and 4b. The pressurizing devices 15a and 15b include movable partition plates 15a1 and 15b1 which close the upper openings of the sample servers 4a, 4b and pressure operating members 15a2 and 15b2 extending from the partition plates 15a1, 15b1 to the outside of the upper openings of the sample servers 4a and 4b. Sample syringes are constituted by the sample servers 4a, 4b and the pressurizing devices 15a, 15b.

A fluid feed control mechanism 5 includes a drive portion 5a which uses a drive source of the valves 18 and that of the pressurizing devices 15 in common.

Next, the operation of the micro fluidics system will be described with reference FIGS. 1 to 4.

The microchip 1 is inserted into a gap between the holder 2 and the base 3, and plural sample servers 4a and 4b which store samples are provided. In this state the sample servers 4a and 4b are provided with the valves 18a, 18b and the pressurizing devices 15a, 15b.

The sample servers 4a, 4b are installed at predetermined positions on the microchip 1. That is, the sample servers 4a and 4b are installed on the microchip 1 so as to provide a closed state between the sample efflux portions of the sample servers 4a, 4b and the sample introducing portions 14a, 14b of the microchip 1 by the valves 18a1 and 18b1. More specifically, the valve bodies 18a1 and 18b1 are positioned within the sample servers 4a and 4b to close the openings of the sample introducing portions 14a and 14b of the microchip 1 and is put in abutment against the surface of the microchip 1.

The microchip device 50 in such a state is installed onto the stage 6 mechanically or by manual operation as in FIG. 1 and an automatic operation is performed.

For performing a treatment, first the valve body 18a1 which closes communication paths between the sample efflux portion of the sample server 4a and the sample introducing portion 14a of the microchip 1 is opened to provide communication between the interior of the sample server 4a and that of the sample introducing portion 14a. The valve body 18a1 is operated by locking the drive portion 5a of the fluid feed control mechanism 5 to an upper end of the operating member 18a2 and moving it upward.

With the valve body 18a1 open, the sample present within the sample server 4a is pressurized by the partition plate 15a1 of the pressurizing device 15a to feed the sample from the sample efflux portion of the sample server 4a to the sample introducing portion 14a, the channel introducing portion 10a of the microchannel 10 and the channel reaction vessel portion 13 as a treating portion in this order. The partition plate 15a1 is operated by pushing and moving downward an upper end of the operating member 15a2 through the drive portion 5a of the fluid feed control mechanism 5. At this time, the amount of fluid fed per unit time to the sample introducing portion 14a can be increased by increasing the descending speed of the fluid feed control mechanism 5, while conversely the amount of fluid fed per unit time to the sample introducing portion 14a can be made very small by decreasing the descending speed of the fluid feed control mechanism 5. Thus it is possible to control the amount to fluid to be fed.

Further, the supply of electric power to the Peltier element 7 is controlled while measuring the surface temperature of the microchip 1. In this way the sample fed is treated in the channel rector portion 13.

After the feed of sample to the microchip 1 is over, the valve body 18a1 is closed. The valve body 18a1 is operated by bringing the drive portion 5a of the fluid feed control mechanism 5 into abutment against the upper end of the operating member 18a2 and moving it downward.

A treatment condition is detected by the treatment condition detector 8, and when this treatment is over, the valve body 18b1 disposed between the sample efflux portion of the sample server 4b and the sample introducing portion 14b of the microchip 1 is opened to provide communication between the sample efflux portion and the sample introducing portion 14b. The valve body 18b1 is operated by locking the drive portion 5a of the fluid feed control mechanism 5 to the upper end of the operating member 18a2 and moving it upward.

With the valve body 18b1 open, the sample present within the sample server 4b is pressurized by the partition plate 15b of the pressurizing device 15b to feed the sample from the sample efflux portion of the sample server 4b to the sample introducing portion 14b, the channel introducing portion 10a and the channel reactor portion 13 in this order. The sample thus fed is treated in the channel reactor portion 13. The partition plate 15b1 is operated by pushing and moving downward an upper end of the operating member 15b2 through the drive portion 5a of the fluid feed control mechanism 5. At this time, the sample introduced is fed to the microchannel reactor portion 13, but tends to advance also to the sample server 4a. However, since the sample introducing portion 14a is sealed with the valve body 18a1, there is no fear that the sample present within the sample server 4a and the sample which has advanced into the sample introducing portion 14a may be mixed together in any other place than the microchannel reactor portion 13.

After the feed of sample to the microchip 1 is over, the valve body 18b1 is closed. The valve body 18b1 is operated by bringing the drive portion 5a of the fluid feed control mechanism 5 into abutment against the upper end of the operating member 18b2 and moving it downward.

During the above treatment, if air bubbles are mixed into the sample with which the channel reactor portion 13 is filled, resulting in an increase of flow path resistance and the sample becoming difficult to flow, evacuation is performed from the drain 9. Even if the evacuation is performed, there is no fear of leakage of the samples stored in the sample servers 4a and 4b. For performing the evacuation, the valves 18a1 and 18b1 are closed and a treatment path formed by the microchannel 10 and the channel reactor portion 13 is evacuated from a fluid outlet port of the drain 9 located on the efflux side.

According to this embodiment the introducing pressure at the time of introducing the samples stored within the sample servers 4a and 4b into the microchip 1 can be controlled to a desired pressure by the pressurizing devices 15 and the amount of the samples introduced per unit time can be controlled accurately. Besides, the feed of the samples by the pressurizing devices 15 is performed in accordance with a differential pressure method and even such samples as non-polar organic solvents can be introduced into the microchip device 50, so that the application range of samples can be expanded in comparison with the electrophoretic method.

Moreover, since the samples stored in the sample servers 4a, 4b and the samples present in the sample introducing portions 14a, 14b are blocked from each other by the valves 18a1 and 18b1, there does not occur mixing of fluid into the samples.

Moreover, since the flow paths from the sample servers 4a and 4b with samples injected therein in a predetermined certain amount up to the sample introducing portions 14a and 14b of the microchip 1 are short, it is not necessary to use conventional tubes or the like for connection between them, nor is it necessary to use a large amount of samples for filling up the interiors of tubes. Therefore, it is also possible to prevent deterioration of samples caused by a change with the passage of time which is attributable to staying of the samples within such tubes.

Figure 5:
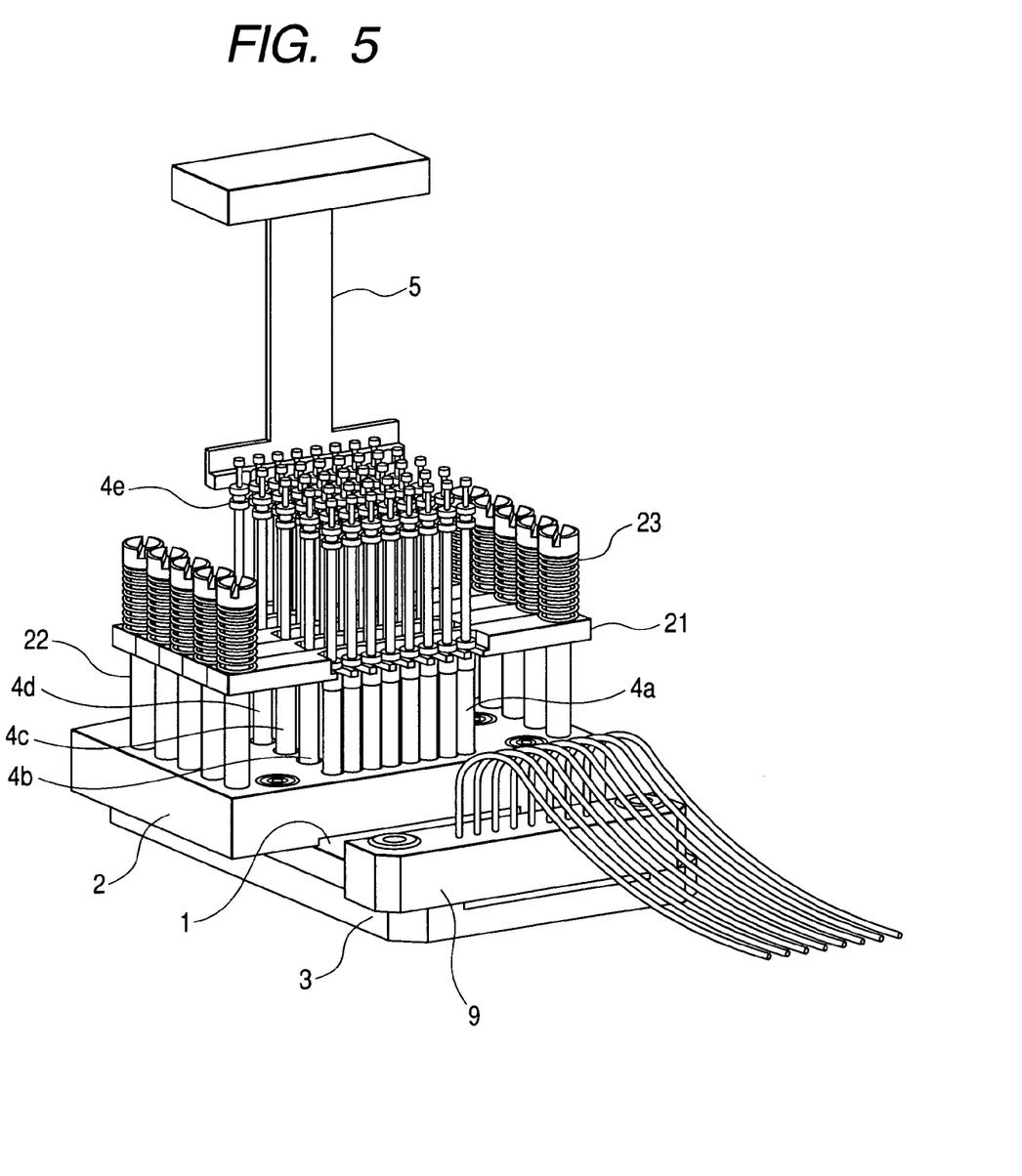
FIG. 5 is a schematic perspective view of a principal portion of a micro fluidics system according to a second embodiment of the present invention.
Figure 6:
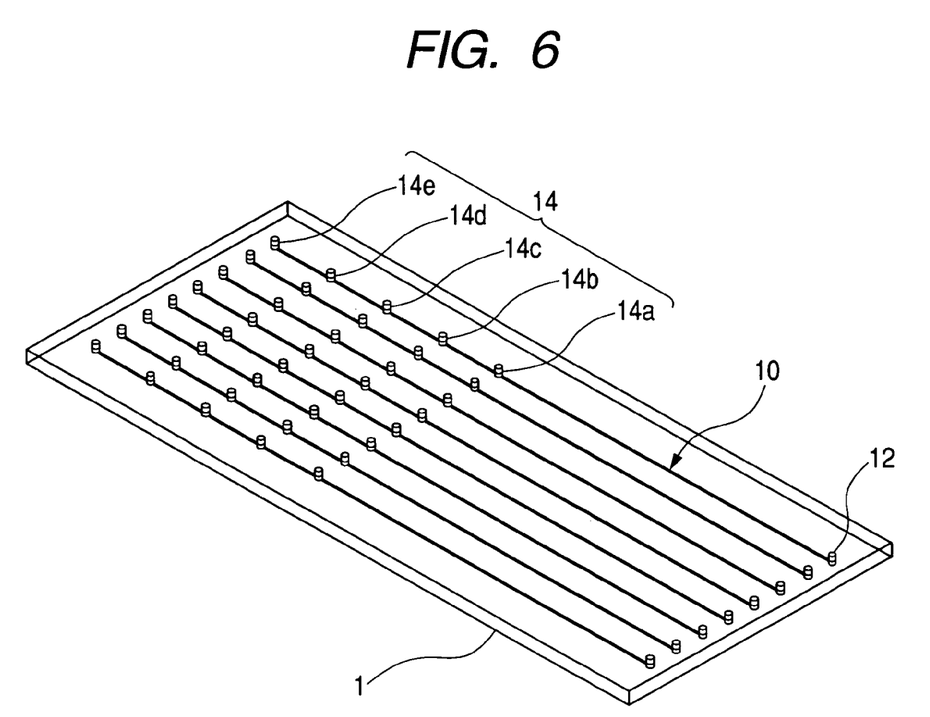
FIG. 6 is a schematic perspective view of a microchip shown in FIG. 5.
Figure 7:
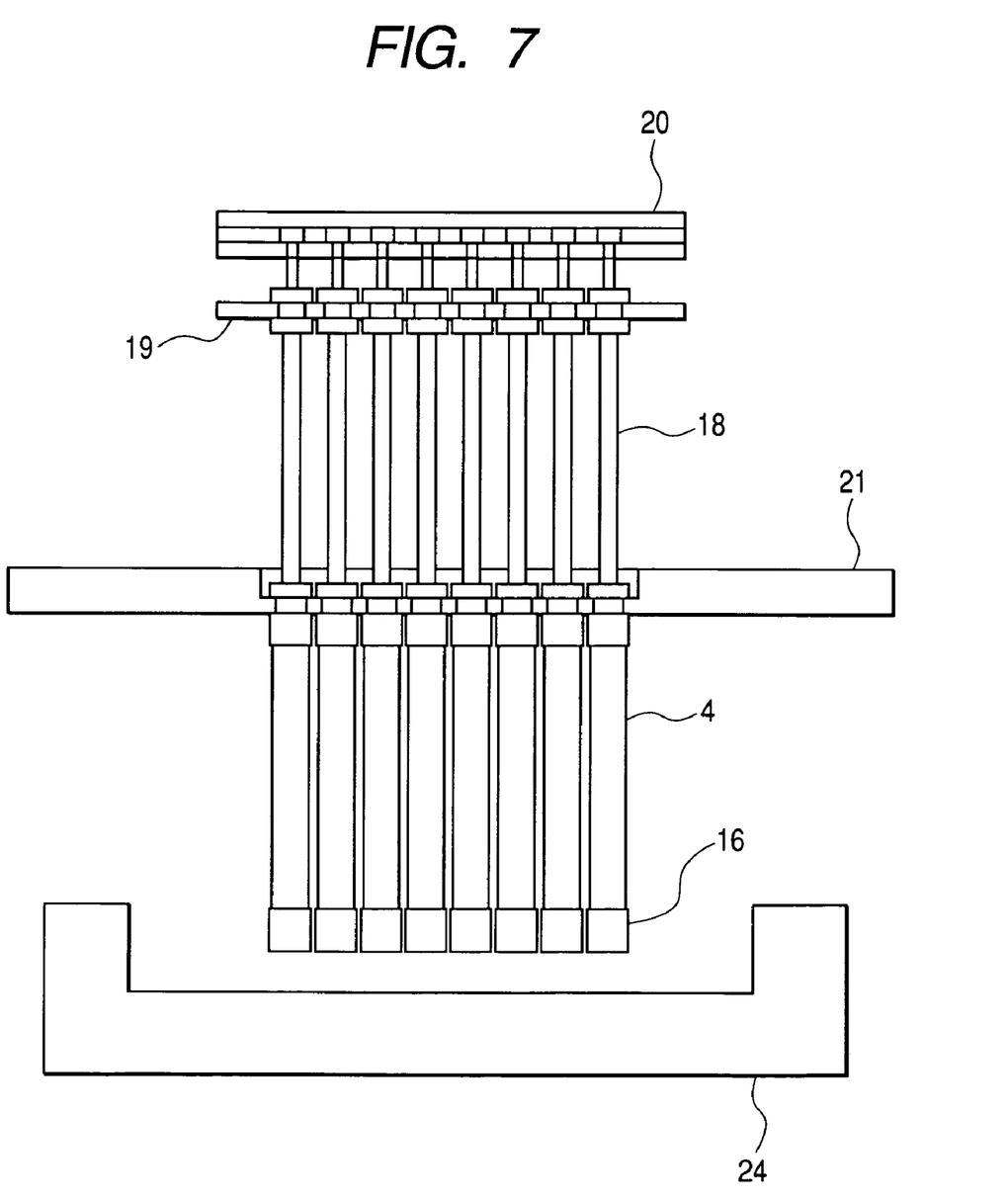
FIG. 7 is a schematic front view of a principal portion showing sample servers about to be filled with samples which sample servers are used in the micro fluidics system shown in FIG. 5.

Next, a second embodiment of the present invention will be described with reference to FIGS. 5 to 7, of which FIG. 5 is a schematic perspective view of a principal portion of a micro fluidics system according to a second embodiment of the present invention, FIG. 6 is a schematic perspective view of a microchip shown in FIG. 5, and FIG. 7 is a schematic front view of a principal portion showing a state in which sample servers used in the micro fluidics system of FIG. 5 are being filled with samples. This second embodiment is different in the following point from the first embodiment and the other points are basically the same as in the first embodiment.

A microchip 1 according to this second embodiment is provided with two or more microchannels 10. In FIG. 6, eight microchannels 10 are provided in parallel. On each of the microchannels 10 there are formed two or more microchip introducing portions 14, and also formed are at least one channel reactor portion and at least one channel separating portion though not shown in FIG. 6. As in the first embodiment, fine solid particles are present in the channel reactor portion. In this embodiment, five sample introducing portions 14 comprising sample introducing ports 14a to 14e are provided for mixing five kinds of samples.

For performing an antigen-antibody reaction with use of the microchip 1, sample servers 4a to 4e each capable of being filled with 1 to 100 μL of sample are used in the example shown in FIG. 5. A sample, a washing solution, an antibody, a washing solution, and a labeled antibody, are charged beforehand into the sample servers 4a, 4b, 4c, 4d, and 4e, respectively. At this time, since there are eight microchannels 10 in the microchip 1, if samples different in antigen concentration are charged into the eight sample servers 4a respectively, eight types of antigen-antibody reactions can be performed by a single analysis work and, after the reactions, measurement can be conducted by a detecting mechanism not shown in FIG. 5.

In case of charging the same sample into all of the eight sample servers 4, the sample servers 4 are fitted in a groove portion of a server connecting bar 21 as shown in FIG. 7, then in this interconnected state of the sample servers, a movable partition plate connecting bar 19 is moved upward in FIG. 7, and if for example a schale 24 is filled with the sample in question, the eight sample servers 4 can be replenished with the sample simultaneously from their discharge ports by movable partition plates 15.

In FIG. 5, with use of guides 22 having threaded front ends, the servers 4 interconnected by the server connecting bar 21 are connected to the holder 2 so as to be fitted in holes for sample servers formed in the holder 2 and be set to the holder. Further, in order to effect sealing positively with packings 16 as explained previously in connection with FIG. 3, the server connecting bar 21 is pushed downward by means of springs 23, whereby the sample servers 4 fitted in the groove are pushed downward and so are the packings 16. Consequently, sealing can be effected positively with respect to the microchip introducing portions 14 provided in the microchip 1.

As shown in FIG. 5, for operating eight sample servers 4 with use of one fluid feed control mechanism 5, if grooves are formed beforehand so as to permit operation of the sample servers like a rake, plural pressurizing devices 15 and valves 18 can be operated at a time. When it is desired to introduce samples in different amounts, by changing the diameters of the sample servers 4, it is possible to attain the feed of fluid to the microchannels 10 from the microchip introducing portions 14 in amounts ranging from 1 to 100 μL/min for example.

Figure 2:
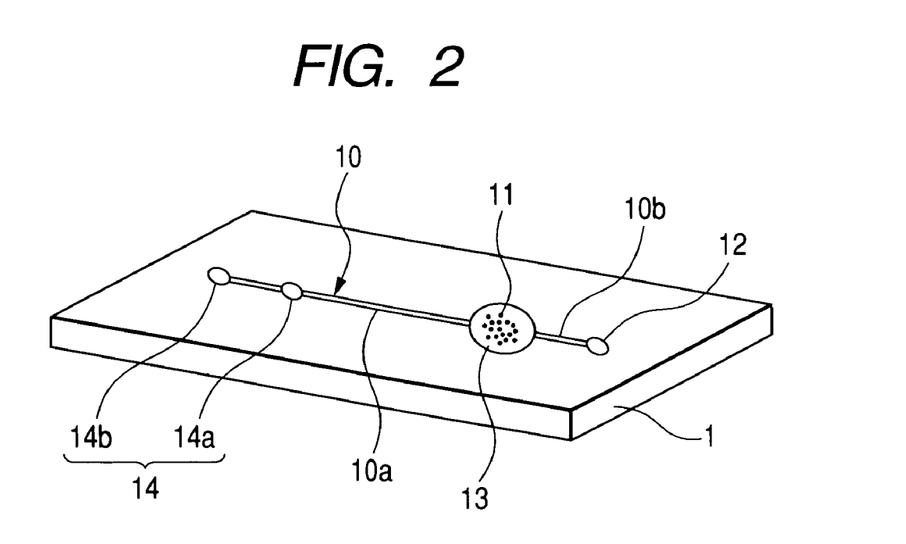
FIG. 2 is an explanatory perspective view of a microchip used in the micro fluidics system shown in FIG. 1.

Reaction is performed in such a procedure as shown in FIG. 2. That is, fine solid particles 11 with antibody supported thereon beforehand are placed in the microchannel reactor portion 13 and the microchip introducing portions 14 are sealed with all the valves 18. The valve 18a of the sample server 4a is operated upward by the fluid feed control mechanism 5, allowing the sample introducing portion 14a to become open, thereafter, the partition plate 15a is moved downward by operating the fluid feed control mechanism 5 downward, causing the sample stored in the sample server 4a to be fed into the associated microchannel 10 from the sample introducing portion 14a, so that a desired antigen contained in the sample binds to the antibody supported on the fine solid particles 11. Next, the same operations as above are repeated to feed the washing solution stored in the sample server 4b into the microchannel 10 from the sample introducing portion 14b, thereby removing unnecessary sample remaining in the microchannel 10. Subsequently, the sample servers 4c and 4d are operated in the same manner and finally the labeled antibody is fed by the sample server 4e, whereby the antibody bound to the fine solid particles 11 and the labeled antibody react with each other. By measuring substance separated from the fine solid particles 11 it is possible to measure the concentration of a specific antigen contained in the sample. Where required at this time, the interior of the microchannel 10 is evacuated by the drain 9, whereby it is possible to remove air bubbles contained between the fine solid particles 11 and prevent a pressure loss resulting from such air bubbles.

What is claimed is:

1. A micro fluidics system comprising:
    a sample server comprising a plurality of sample server portions storing a plurality of different kinds of samples, each of the sample server portions having a sample efflux portion provided on a side of the sample server portion and having a lower opening;
    a microchip provided as a separate member from the sample server and including a plurality of sample introducing portions in the microchip having upper openings in an upper surface of the microchip communicating with the lower openings of respective ones of the sample efflux portions, a treating portion allowing the samples to be subjected to a predetermined treatment, and a microchannel connecting the sample introducing portions and the treatment portion,
    wherein the sample server is installed on the microchip so that the lower openings of the sample efflux portions cover respective ones of the upper openings of the sample introducing portions; and
    a sample feeder for feeding the samples stored in the sample server to the sample introducing portions through the sample efflux portions,
    wherein the sample feeder comprises a plurality of valves for opening and closing communication paths between the sample efflux portions of the sample server and the sample introducing portions of the microchip by opening and closing the upper openings of the sample introducing portions with respective ones of valve bodies of the valves, and a plurality of pressurizing devices, which are provided respectively for the sample server portions, for pressurizing the samples stored in the sample server portions in an open condition of the valve bodies and pushing them out into the sample introducing portions.

2. A micro fluidics system according to claim 1, wherein the sample server includes cylindrical bodies whose one ends are open larger than the sample introducing portions and whose opposite ends are closed, the cylindrical bodies being installed so that the one ends thereof come into abutment against the microchip, allowing the openings thereof to cover the openings of the sample introducing portions, and the valves are positioned within the sample server to open and close the openings of the sample introducing portions and are installed so as to come into abutment against the surface of the microchip.

3. A micro fluidics system according to claim 1, further comprising a fluid feed control mechanism having a drive portion, the drive portion using a drive source of the valves and a drive source of the pressurizing devices in common.

4. A micro fluidics system according to claim 3, wherein the sample server includes cylindrical bodies which are open on both sides thereof, the pressurizing devices include partition plates which close one end sides of the cylindrical bodies and which are disposed movably and operating members extending from the partition plates to the exterior of one openings of the cylindrical bodies, the valves include valve bodies disposed on the other opening sides of the cylindrical bodies and operating members extending from the valve bodies to the exterior of the other openings of the cylindrical bodies through the partition plates, and the fluid feed control mechanism includes the drive portion which actuates the operating members of the pressurizing devices and the operating members of the valves in an alternate manner.

5. A micro fluidics system according to claim 1, wherein a drain for storing the samples treated by the microchip is attached to the microchip.

6. A micro fluidics system according to claim 1, wherein the microchip includes a plurality of independent treatment paths each constituted by the sample introducing portions, the microchannel and the treating portion.

7. A micro fluidics system according to claim 6, wherein the microchip is formed by a multitude of independent rows of the treatment paths, and the sample server is formed independently and correspondingly to each of the rows of the treatment paths, is supported through a common connecting member and is installed in the microchip removably.

8. A treating method using a micro fluidics system, comprising the steps of:

providing a microchip including a plurality of sample introducing portions in the microchip having upper openings in an upper surface of the microchip, a treating portion allowing the samples to be subjected to a predetermined treatment, and a microchannel connecting the sample introducing portions and the treatment portion;

providing a sample server comprising a plurality of sample server portions storing a plurality of different kinds of samples, each of the sample server portions having a sample efflux portion provided on a side of the sample server portion and having a lower opening;

installing the sample server on the microchip so that the lower openings of the sample efflux portions cover respective ones of the upper openings of the sample introducing portions, in a condition of closing communication paths between the sample efflux portions in the sample server and the sample introducing portions in the microchip by means of valves for opening and closing communication paths between the sample efflux portions of the sample server and the sample introducing portions of the microchip by opening and closing the upper openings of the sample introducing portions with respective ones of valve bodies of the valve opening the valve concerned between the associated sample efflux portion in the sample server and the associated sample introducing portion in the microchip, allowing the sample efflux portion and the sample introducing portion to communicate with each other, pressurizing a sample by means of pressurizing devices, feeding the pressurized sample from the sample efflux portion to the sample introducing portion, the microchannel and the treating portion in this order;

closing the open valve, thereafter opening the valve concerned between another associated sample efflux portion in the sample server and another associated sample introducing portion in the microchip, allowing the sample efflux portion and the sample introducing portion to communicate with each other, pressurizing another sample by pressurizing devices, feeding the pressurized sample from the sample efflux portion to the sample introducing portion, the microchannel and the treating portion in this order; and allowing the sample to be treated in the treating portion.

9. A treating method using a micro fluidics system according to claim 8, wherein all of the valves are brought into a closed condition and a treatment path formed by the sample introducing portions, the microchannel and the treating portion is evacuated from an efflux side of the treating portion.

* * * * *